United States Patent
Nakamura

(10) Patent No.: US 9,144,407 B2
(45) Date of Patent: Sep. 29, 2015

(54) IMAGE PROCESSING DEVICE AND METHOD, AND PROGRAM

(75) Inventor: Keigo Nakamura, Kanagawa-ken (JP)

(73) Assignee: FUJIFILM CORPORATION, Tokyo (JP)

( * ) Notice: Subject to any disclaimer, the term of this patent is extended or adjusted under 35 U.S.C. 154(b) by 394 days.

(21) Appl. No.: 12/737,702

(22) PCT Filed: Mar. 30, 2010

(86) PCT No.: PCT/JP2010/002306
§ 371 (c)(1),
(2), (4) Date: Feb. 8, 2011

(87) PCT Pub. No.: WO2010/113479
PCT Pub. Date: Oct. 7, 2010

(65) Prior Publication Data
US 2011/0131528 A1    Jun. 2, 2011

(51) Int. Cl.
*A61B 6/00*        (2006.01)
*A61B 6/03*        (2006.01)
*G06T 11/00*    (2006.01)

(52) U.S. Cl.
CPC ............... *A61B 6/032* (2013.01); *A61B 6/037* (2013.01); *A61B 6/465* (2013.01); *A61B 6/563* (2013.01); *G06T 11/008* (2013.01)

(58) Field of Classification Search
CPC .......................... G06T 7/0012; G06T 11/003
USPC ............ 378/21; 382/128, 131; 715/810, 811, 715/812, 825
See application file for complete search history.

(56) References Cited

U.S. PATENT DOCUMENTS

| | | | | |
|---|---|---|---|---|
| 6,500,118 | B1 * | 12/2002 | Hashimoto | 600/437 |
| 6,608,650 | B1 * | 8/2003 | Torres et al. | 348/333.02 |
| 7,245,747 | B2 * | 7/2007 | Oosawa | 382/128 |
| 8,295,568 | B2 * | 10/2012 | Sakaida | 382/128 |
| 2004/0100505 | A1 * | 5/2004 | Cazier | 345/811 |
| 2005/0256402 | A1 * | 11/2005 | Kawashima et al. | 600/437 |
| 2006/0008143 | A1 * | 1/2006 | Truyen et al. | 382/173 |

(Continued)

FOREIGN PATENT DOCUMENTS

| | | |
|---|---|---|
| JP | 2002-253539 | 9/2002 |
| JP | 2003-010166 | 1/2003 |

(Continued)

OTHER PUBLICATIONS

Office Action issued by the Australian Patent Office on Oct. 29, 2014 in connection with Australian Patent Application No. 2010231365.

*Primary Examiner* — Steven Sax
*Assistant Examiner* — David Choi
(74) *Attorney, Agent, or Firm* — Jean C. Edwards, Esq.; Edwards Neils PLLC

(57) ABSTRACT

An image obtaining unit obtains a three-dimensional image, which is formed by a plurality of tomographic images obtained by carrying out tomographic imaging of a subject, and a part information obtaining unit obtains information of a result of part recognition of the subject contained in the three-dimensional image. A menu specifying unit specifies, from a plurality of menus used to display the three-dimensional image, a menu depending on a part based on the information of the result of part recognition, and a display control unit displays the specified menu on a display unit.

7 Claims, 12 Drawing Sheets

(56) References Cited

U.S. PATENT DOCUMENTS

| | | | |
|---|---|---|---|
| 2006/0064321 A1* | 3/2006 | Sasano et al. | 705/2 |
| 2007/0025508 A1* | 2/2007 | Ohishi | 378/62 |
| 2007/0195061 A1* | 8/2007 | Nakamura | 345/158 |
| 2007/0269089 A1* | 11/2007 | Sakaida | 382/128 |
| 2008/0260226 A1* | 10/2008 | Moriya | 382/128 |
| 2008/0267481 A1* | 10/2008 | Nakamura | 382/131 |
| 2011/0131528 A1* | 6/2011 | Nakamura | 715/810 |

FOREIGN PATENT DOCUMENTS

| | | |
|---|---|---|
| JP | 2003-284705 | 10/2003 |
| JP | 2005-034473 | 2/2005 |
| JP | 2006-061278 | 3/2006 |
| JP | 2007-185429 | 7/2007 |
| JP | 2008-253681 | 10/2008 |
| JP | 2008-259682 | 10/2008 |
| JP | 2008-259710 | 10/2008 |

* cited by examiner

FIG.2

| PART | ANALYSIS APPLICATION |
|---|---|
| HEAD | BRAIN BLOOD VESSEL EXTRACTION |
| NECK | BRAIN BLOOD VESSEL EXTRACTION |
| CHEST | LUNG ANALYSIS, CORONARY ARTERY ANALYSIS, CARDIAC FUNCTION ANALYSIS, CALCIFICATION SCORE |
| CHEST-ABDOMEN | LUNG ANALYSIS, LIVER ANALYSIS |
| ABDOMEN | LIVER ANALYSIS, LARGE INTESTINE ANALYSIS |
| PELVIS | LARGE INTESTINE ANALYSIS |

T1

| PATIENT NAME | PATIENT ID | EXAMINATION TIME AND DATE |
|---|---|---|
| XXXX | 01234 | 2009.3.24 |
| YYYY | 01235 | 2009.3.24 |
| ZZZZ | 01236 | 2009.3.24 |
| ⋮ | ⋮ | ⋮ |

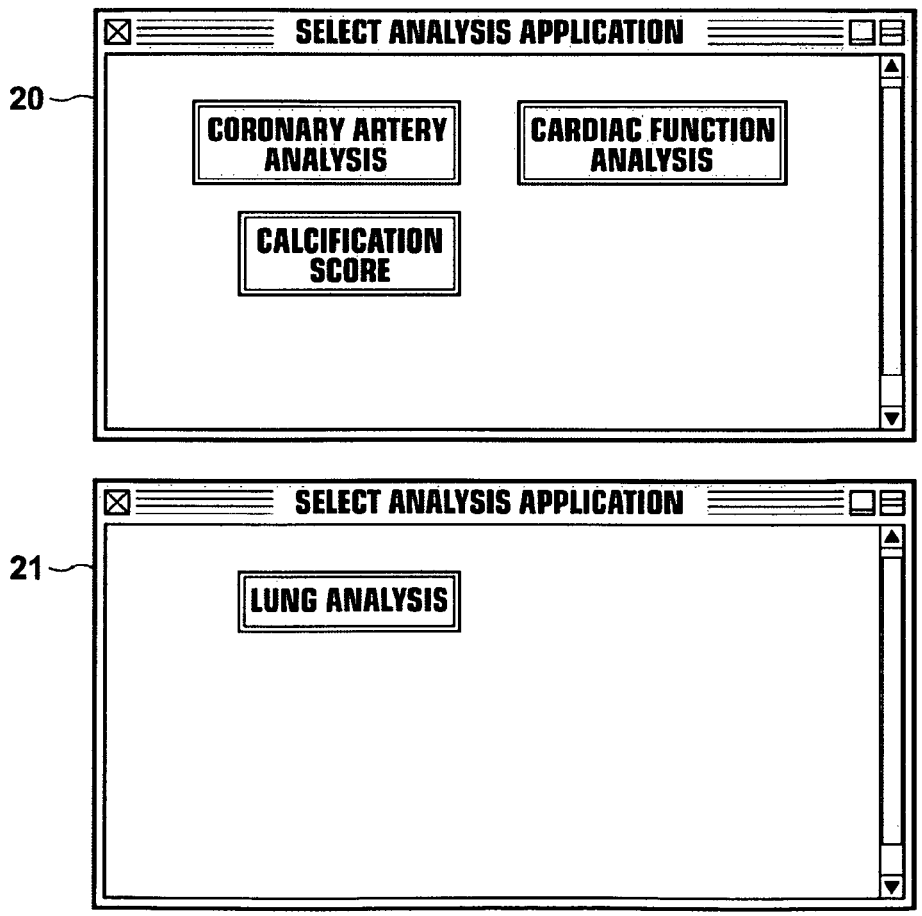

FIG.11
| CHEST | CT SYSTEM | CORONARY ARTERY ANALYSIS, CARDIAC FUNCTION ANALYSIS, CALCIFICATION SCORE |
|---|---|---|
| | MR SYSTEM | CARDIAC FUNCTION ANALYSIS, DELAYED ENHANCED ANALYSIS |
T3
FIG.12
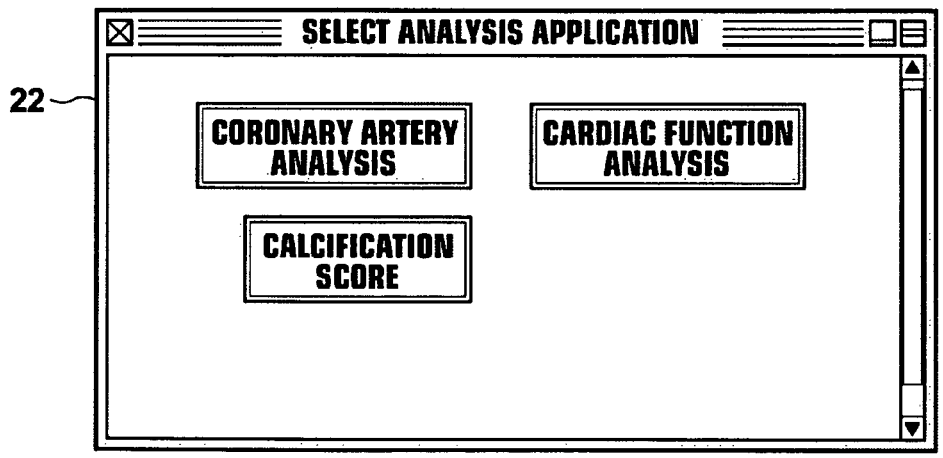
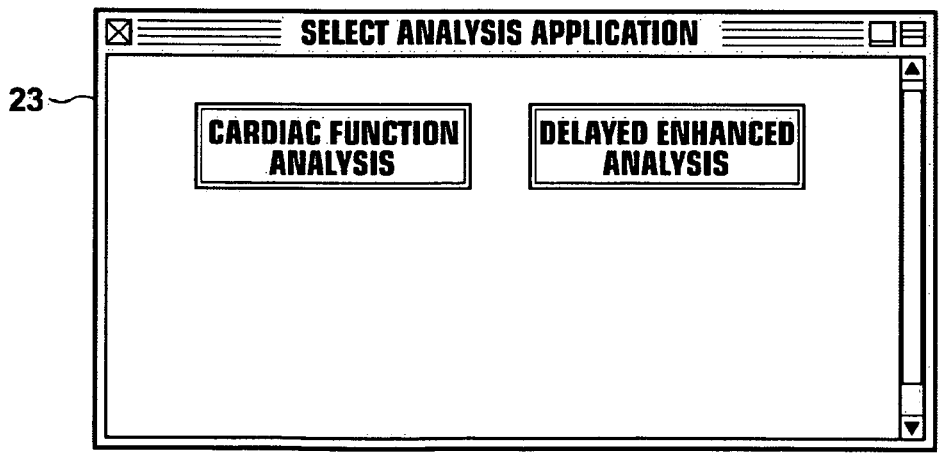

| PART | COLOR TEMPLATE |
|---|---|
| HEAD | P1-P5 |
| NECK | P6-P10 |
| CHEST | P11-P20 |
| CHEST-ABDOMEN | P21-P25 |
| ABDOMEN | P26-P30 |
| PELVIS | P31-P35 |

IMAGE PROCESSING DEVICE AND METHOD, AND PROGRAM

CROSS-REFERENCE TO RELATED APPLICATIONS

The present invention is a 35 U.S.C. 371 National Stage Entry of PCT/JP2010/002306, filed Mar. 30, 2010, which claims priority from Japanese Patent Application No. 2009-083931, filed on Mar. 31, 2009, the contents of all of which are herein incorporated by reference in their entirety. The present application also claims priority from Japanese Patent Application No. 2010-522886, which is the Japanese Phase Application of PCT/JP2010/002306, the contents of all of which are herein incorporated by reference in its entirety.

BACKGROUND OF THE INVENTION

1. Field of the Invention

The present invention relates to an image processing device and an image processing method for processing a three-dimensional image formed by a plurality of tomographic images, which are obtained by tomographic imaging of a subject, as well as a program for causing a computer to carry out the image processing method.

2. Description of the Related Art

In recent years, in the field of medical images, modalities using various technologies, such as an X-ray CT (Computed Tomography) system, an ultra-sound (US) diagnosis system, an MRI (Magnetic Resonance Imaging) system, a PET (Positron Emission Tomography) system, and an SPET (Single-Photon Emission Tomography) system are used, besides an X-ray imaging system. Along with improvement of speed and performance, such as to accommodate multislice technology, of such modalities, it has become possible to image two or more parts of a subject in a series of imaging to obtain several hundreds to several thousands of high-resolution tomographic images. However, it takes time to observe these tomographic images one by one. Further, it requires a trained doctor to understand a three-dimensional shape of a structure to be observed (an organ or a tissue, such as body surface, bone, heart, lung field or liver) only from the tomographic images.

To address this problem, various techniques have been proposed to enhance visibility of the entire structure, and further a lesion contained in the structure, by recognizing a structure of interest, and generating, from tomographic images containing the structure of interest, a three-dimensional image of the structure of interest by analyzing the tomographic images with using a method, such as maximum intensity projection (MIP) or minimum intensity projection (MinIP), to achieve MIP display, or to achieve volume rendering (VR) display of the three-dimensional image.

On the other hand, there are a wide variety of analysis applications for performing such an analysis. Further, besides the analysis applications, there are a wide variety of color templates for changing a shading pattern of a VR display of a three-dimensional image, image processing applications and display applications (which will hereinafter be referred to as analysis applications, etc.). Therefore, the number of menus for selecting the analysis applications, etc., during image interpretation is increased, and a burdensome operation is imposed on the user, such as a reading physician or a technologist, for selecting menu items.

A technique which involves: calculating index values which indicate anatomical characteristics from a medical image; determining whether the imaged subject is an adult, infant, young child or child based on the calculated index values; selecting optimal imaging menu items to be selected from imaging menu items depending on the subject; and displaying only the selected imaging menus has been proposed (see Japanese Patent No. 2007-185429, which will hereinafter be referred to as Patent Document 1). According to the technique disclosed in Patent Document 1, when a medical image is displayed, unnecessary imaging menu items for the imaged subject are not displayed, and thus a burden imposed on the user for selecting the imaging menu items can be reduced.

In the case where tomographic imaging is carried out using the above-described modality, such as a CT system, there are often the cases where two or more body parts are imaged, such as from the chest to the abdomen or from the head to the chest, besides the cases where only a single body part (for example, only the chest or abdomen) is imaged, in a single examination. The above-described analysis applications, etc., are prepared for each body part. Therefore, when two or more body parts are imaged, two or more of the analysis applications, etc., are used for analysis, or the like. Although the technique disclosed in Patent Document 1 allows selection of an optimal imaging menu item depending on the subject, the technique is not applicable to the cases where tomographic images containing two or more parts are obtained, as described above.

SUMMARY OF THE INVENTION

In view of the above-described circumstances, the present invention is directed to reducing a burden imposed on the user for selecting a menu item when a menu used to process a three-dimensional image is displayed, in particular, in the case where tomographic images containing two or more parts are obtained.

An image processing device according to the invention includes:

image obtaining means for obtaining a three-dimensional image, the three-dimensional image being formed by a plurality of tomographic images obtained by carrying out tomographic imaging of a subject;

part information obtaining means for obtaining information of a result of part recognition of the subject contained in the three-dimensional image;

menu specifying means for specifying, from a plurality of menus used to display the three-dimensional image, a menu depending on a part based on the information of the result of part recognition; and display control means for displaying the specified menu on a display means.

A specific example of the "subject" herein may be a human body; however, the subject may be a body of an animal, etc.

In the case where the subject is a human body, the "part" to be recognized herein is a body part of the human body. Specific examples thereof may include head, neck, chest, abdomen, pelvis, legs, and combined parts including adjacent two parts of the above-listed parts, such as head-neck and chest-abdomen.

In the image processing device according to the invention, the part information obtaining means may obtain the information of the result of part recognition by recognizing a part of the subject contained in the three-dimensional image.

In the image processing device according to the invention, the tomographic images may be axial tomographic images, and the tomographic images may contain at least one of a part selected from head, neck, chest, abdomen, pelvis and legs, and a combined part including at least two adjacent parts of head, neck, chest, abdomen, pelvis and legs.

In the image processing device according to the invention, the menu may be a menu used to select an application for analyzing the three-dimensional image.

In the image processing device according to the invention, the menu specifying means may specify the menu depending also on user information of a user who uses the three-dimensional image.

In the image processing device according to the invention, the menu specifying means may specify the menu depending also on a type of a modality used to obtain the three-dimensional image.

In the image processing device according to the invention, the display control means may change a manner of display of the specified menu depending on a frequency of use of each menu.

In the image processing device according to the invention, the display control means may be able to selectively display a particular part contained in the three-dimensional image, and the menu specifying means may specify the menu depending also on the displayed part in the three-dimensional image.

An image processing method according to the invention is an image processing method to be implemented on a computer, including the steps, which are carried out by the computer, of:

obtaining a three-dimensional image, the three-dimensional image is formed by a plurality of tomographic images obtained by carrying out tomographic imaging of a subject;

obtaining information of a result of part recognition of the subject contained in the three-dimensional image;

specifying, from a plurality of menus used to display the three-dimensional image, a menu depending on a part based on the information of the result of part recognition; and displaying the specified menu on a display means.

The image processing method according to the invention may be provided in the form of a program to cause a computer to carry out the image processing method.

According to the present invention, based on a result of part recognition of a subject contained in a three-dimensional image, which is formed by a plurality of tomographic images obtained by carrying out tomographic imaging of the subject, a menu depending on the part is specified from menus used to display the three-dimensional image, and the specified menu is displayed. Therefore, when an instruction to display the three-dimensional image is made, only a menu depending on the part contained in the three-dimensional image is displayed. Thus, it is not necessary for the user, such as a reading physician or a technologist, to make selection from a menu that contains unnecessary menu items corresponding to parts that are not contained in the three-dimensional image, and thus a burden imposed on the user during menu selection can be reduced.

Further, by specifying the menu depending also on user information of a user who uses the three-dimensional image, a menu containing menu items with high frequency of use for the user is displayed, and thus a burden imposed on the user during menu selection can be reduced.

Furthermore, by specifying the menu depending also on a type of a modality used to obtain the three-dimensional image, a menu containing menu items which are highly likely to be used is displayed, and thus a burden imposed on the user during menu selection can be reduced.

Moreover, by changing the manner of display of the specified menu so that a menu item with a higher frequency of use in the specified menu can more easily be selected, a burden imposed on the user during menu selection can be reduced.

Further, by enabling selective display of a particular part contained in the three-dimensional image and specifying the menu depending also on the displayed part in the three-dimensional image, a burden imposed on the user during menu selection can be reduced.

BRIEF DESCRIPTION OF THE DRAWINGS

FIG. 2 is a diagram illustrating an example of a table used in the first embodiment, FIG. 9 is a diagram illustrating an example of a table used in a second embodiment, FIG. 10 is a diagram illustrating a state where a list of an analysis application menu is displayed in the second embodiment, FIG. 11 is a diagram illustrating an example of a table used in a third embodiment, FIG. 12 is a diagram illustrating a state where a list of an analysis application menu is displayed in the second embodiment.

DESCRIPTION OF THE PREFERRED EMBODIMENTS

Figure 1:
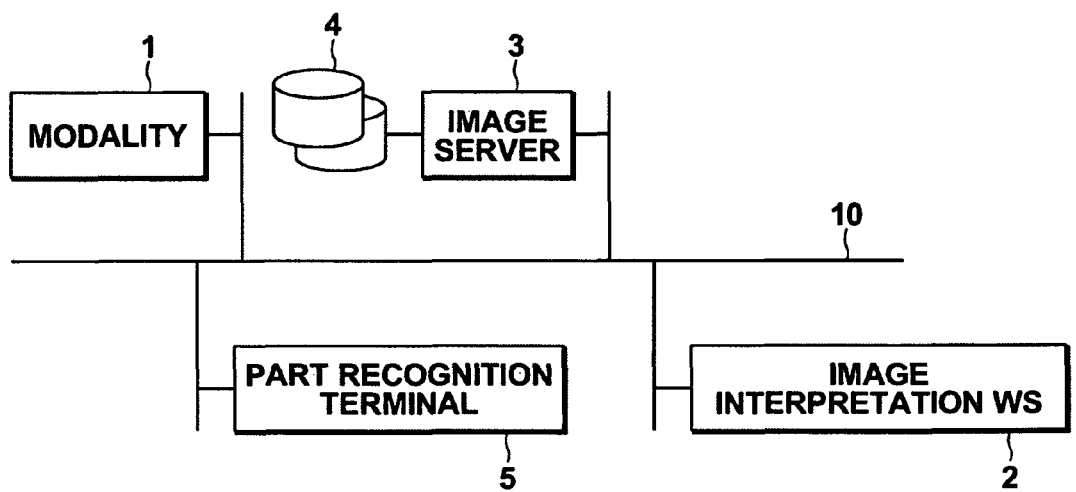
FIG. 1 is a diagram illustrating the schematic configuration of a medical information system, to which an image processing device according to an embodiment of the invention is applied.

Hereinafter, embodiments of the present invention will be described with reference to the drawings. FIG. 1 is a diagram illustrating the schematic configuration of a medical information system, to which an image processing device according to a first embodiment of the invention is applied. As shown in FIG. 1, the medical information system according to the first embodiment includes: an imaging system (modality) 1 for taking a medical image, an image interpretation workstation (WS) 2, an image server 3, an image database 4 and a part recognition terminal 5, which are connected via a network 10 to be capable of communicating with each other. The devices in this embodiment are controlled by a program installed from a recording medium, such as a CD-ROM. Alternatively, the program may be downloaded from a server connected via a network, such as the Internet, to be installed.

The modality 1 includes a system that images a part to be examined of a subject to generate image data of an image representing the part, adds associated information, such as examination information and patient information, to the image data, and outputs the image data. The associated information has a format that conforms to a standard, such as the DICOM standard, and to specifications of the manufacturer of the modality, etc. Specific examples of the modality 1 include a CT system, an MRI system, a PET system, an SPET system and an ultrasonographic imaging system. In this embodiment, it is assumed that the image data is image data of a three-dimensional image representing a part to be examined of a subject, which is obtained with a CT system, and is in the form of collective data of axial tomographic images (hereinafter, tomographic images) taken at predetermined slice intervals and with a predetermined slice thickness; however, this is not intended to limit the invention. Although one modality 1 is shown in FIG. 1, two or more types of modalities 1 may be connected.

The image interpretation workstation 2 is used by the user, such as a reading physician or a technologist, to carry out image interpretation and generate an image interpretation report. The image interpretation workstation 2 includes a processor, one or two high-definition displays, and an input device, such as a keyboard and a mouse, or a touch panel. The image interpretation workstation 2 carries out various operations, such as sending a request to view an image to the image server 3, applies various types of image processing to an image received from the image server 3, carrying out various types of analysis processing, including automatic detection and highlighting of an area likely to be a structure or a lesion in an image, displaying an image, assisting the user to generate an image interpretation report, sending a request to register an image interpretation report and a request to view an image interpretation report to an image interpretation report server (not shown) and displaying an image interpretation report received from the image interpretation report server.

The image interpretation workstation 2 has analysis applications installed thereon, which are used to carry out various types of analysis processing instructed by the user. The analysis applications are prepared correspondingly to parts contained in three-dimensional images. In this embodiment, the image interpretation workstation 2 stores a table that associates each part contained in the three-dimensional images with a type(s) of analysis application(s) used for analysis of the part. FIG. 2 is a diagram illustrating an example of the table used in the first embodiment. As shown in FIG. 2, the table T1 associates each part with a type(s) of analysis application(s). Specifically, the head and the neck are associated with an analysis application of brain blood vessel extraction, the chest is associated with analysis applications of lung analysis, coronary artery analysis, cardiac function analysis and calcification score, the chest-abdomen is associated with analysis applications of lung analysis and liver analysis, the abdomen is associated with analysis applications of liver analysis and large intestine analysis, and the pelvis is associated with an analysis application of large intestine analysis.

When the user performs image interpretation, the image interpretation workstation 2 first obtains, in response to an instruction from the user, the associated information and information of a result of part recognition, which will be described later, for each examination. Then, the image interpretation workstation 2 references the table T1 based on the obtained information of the result of part recognition to specify the analysis application depending on the part contained in the three-dimensional image, and displays the specified analysis application on a display. Display of the specified analysis application will be described later.

A criterion to determine whether or not a certain part is contained in the three-dimensional image may be such that, if the certain part is contained in at least one of the tomographic images forming the three-dimensional image, it is determined that the part is contained in the three-dimensional image. Alternatively, if the certain part is contained across at least a predetermined distance (the number of tomographic images× slice interval) along the body axis direction, it may be determined that the part is contained in the three-dimensional image. For example, if the neck is contained across a distance of at least 10 cm, it may be determined that the neck is contained in the three-dimensional image. In this case, if the neck is contained across a distance of only 5 cm, no analysis application associated with the neck is specified.

The image server 3 is formed by a general-purpose computer having a relatively high processing capacity with a software program that provides a function of a database management system (DataBase Management System: DBMS) installed thereon. The image server 3 includes a large capacity storage forming the image database 4. The storage may be a large capacity hard disk device connected to the image server 3 via a data bus, or may be a disk device which is connected to a NAS (Network Attached Storage) and a SAN (Storage Area Network) connected to the network 10. The image server 3 is also provided with a communication interface for communication with the modality 1, the image interpretation workstation 2, etc., over the network 10.

When the image server 3 receives a request to register an image from the modality 1, the image server 3 converts the image into a format for the database and registers the image in the image database 4. Further, the information of the result of part recognition obtained by the part recognition terminal 5, which will be described later, is registered in the image database 4.

In the image database 4, the above-described image data of the three-dimensional image, the associated information, and the information of the result of part recognition, which will be described later, are registered. The associated information may contain, for example, an image ID for identifying each image, a patient ID for identifying each subject, an examination ID for identifying each examination, a unique ID (UID) assigned to each image, an examination date and time when each image is generated, a type of modality used in an examination to obtain each image, patient information, such as name, age, sex, etc., of each patient, examined part (imaged part), imaging information (such as imaging protocol, imaging sequence, imaging technique, imaging conditions, whether or not a contrast agent is used, etc.), a serial number or a collection number when a plurality of images are obtained in a single examination, etc.

Further, when the image server 3 receives a request to view an image from the image interpretation workstation 2 over the network 10, the image server 3 searches for the image registered in the image database 4, and sends the image extracted by the search to the image interpretation workstation 2 which has sent the request.

When the user, such as a reading physician or a technologist, makes an operation to request to view an image to be interpreted, the image interpretation workstation 2 sends a request to view to the image server 3, and obtains the image necessary for image interpretation. Then, in response to a request by the user, the image interpretation workstation 2 carries out analysis processing, such as automatic detection of a lesion, on the image.

Before or after the three-dimensional image, which is formed by tomographic images obtained at the modality 1, is registered in the image database 4, the part recognition terminal 5 carries out a part recognition process for recognizing a part of the subject contained in the three-dimensional image. The part recognition terminal 5 is also provided with a communication interface for communication with the modality 1, the image interpretation workstation 2, etc., over the network 10. When the part recognition terminal 5 has received a notification from the image server 3 notifying that the registration of the three-dimensional image into the image database 4 has been completed, the part recognition terminal 5 starts the recognition process. Alternatively, the part recognition terminal 5 may start the recognition process in response to an instruction fed from the image interpretation workstation 2.

Now, the part recognition process carried out by the part recognition terminal 5 is described. The part recognition may be achieved using a technique disclosed, for example, in Japanese Unexamined Patent Publication No. 2008-259682. The technique disclosed in Japanese Unexamined Patent Publication No. 2008-259682 involves: normalizing inputted tomographic images; calculating a number of feature quantities from the normalized tomographic images; inputting the feature quantities calculated for each normalized tomographic image to a classifier, which is obtained by using an AdaBoost technique, to calculate, for each part, a score indicating a likelihood of being the part; and determining the part shown in each tomographic image based on the calculated part scores using dynamic programming so that the order of the body parts of a human body is maintained. Further, a method using color template matching (see, for example, Japanese Unexamined Patent Publication No. 2002-253539) or a method using eigenimages of each part (see, for example, Japanese Unexamined Patent Publication No. 2003-010166) may be used. In this manner, the part is recognized for each tomographic image, and a result of part recognition is obtained for each tomographic image.

The part recognition terminal 5 sends the information of the result of part recognition to the image server 3. The image server 3 registers the received information of the result of part recognition in the image database 4, and sends the information of the result of part recognition together with the three-dimensional image from the image server 3 to the image interpretation workstation 2 in response to an instruction fed from the image interpretation workstation 2.

Figures 3, 4:
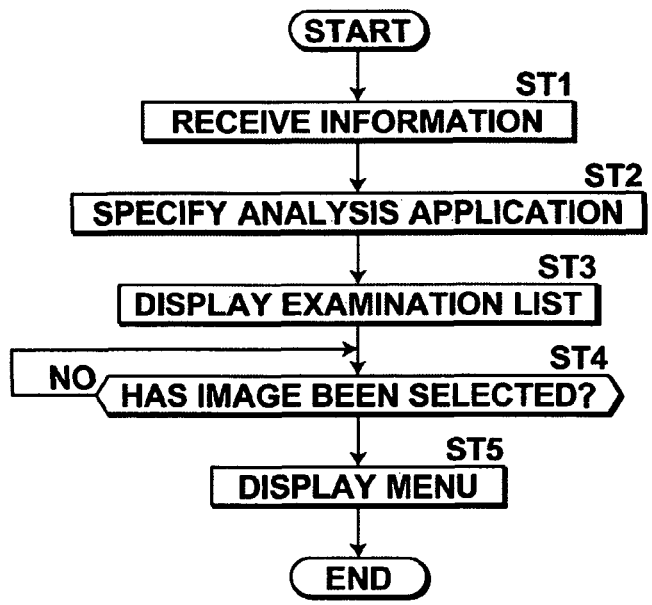
FIG. 3 is a flow chart illustrating a process carried out in the first embodiment.
FIG. 4 is a diagram illustrating a displayed examination list.

Next, a process carried out in the first embodiment is described. FIG. 3 is a flow chart illustrating the process carried out in the first embodiment. The process described here includes operations that are carried out after the information of the result of part recognition has been registered in the image database 4, and the user, such as a reading physician, has fed an instruction of image interpretation to the image interpretation workstation 2, and until the specified analysis application menu is displayed. When the user has fed the instruction of image interpretation to the image interpretation workstation 2, the image server 3 reads out a registered three-dimensional image together with the associated information and the information of the result of part recognition thereof from the image database 4, and sends the three-dimensional image, the associated information and the information of the result of part recognition to the image interpretation workstation 2.

The image interpretation workstation 2 receives the three-dimensional image, the associated information and the information of the result of part recognition ("receive information" instep ST1). Then, based on the received information of the result of part recognition, the analysis application(s) is specified depending on the part contained in the three-dimensional image with referencing the above-described table T1 (step ST2), and an examination list is displayed on a display based on the associated information (step ST3).

FIG. 4 is a diagram illustrating the displayed examination list. As shown in FIG. 4, the examination list includes information of patient name, patient ID and examination time and date based on the associated information associated with each obtained three-dimensional image. The image interpretation workstation 2 starts monitoring to determine whether or not the user has clicked the right mouse button to select an image from the examination list (step ST4). If an affirmative determination is made in step ST4, a pop-up of a menu corresponding to the analysis application(s) specified for the selected image is displayed (step ST5), and the process ends.

Figure 5:
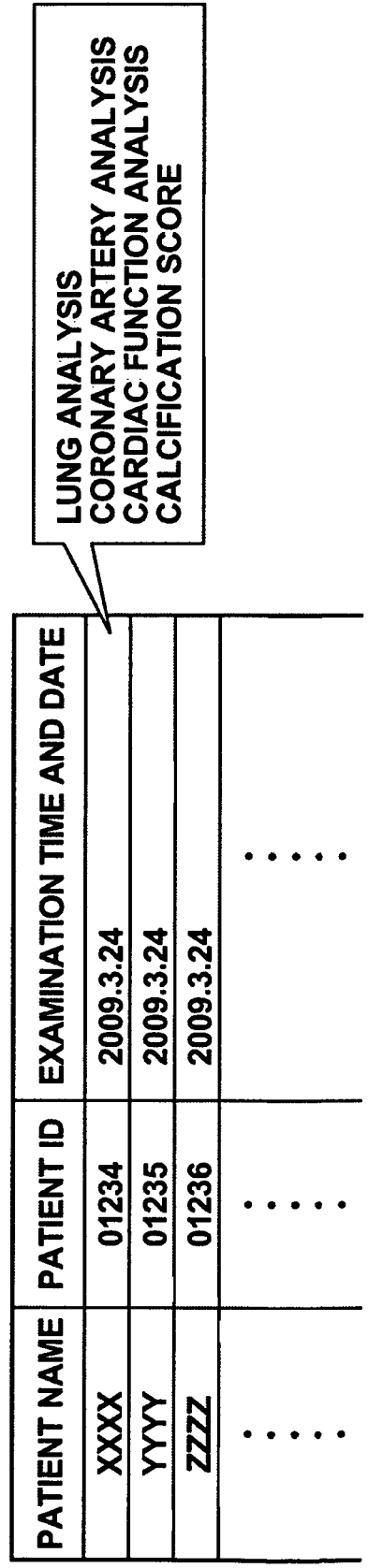
FIG. 5 is a diagram illustrating a state where a pop-up of an analysis application menu is displayed in the first embodiment.

FIG. 5 is a diagram illustrating a state where the pop-up of the analysis application menu is displayed. As shown in FIG. 5, in the case where the result of part recognition of the selected image is the chest, the analysis applications of lung analysis, coronary artery analysis, cardiac function analysis and calcification score are specified, and the pop-up of the menu containing the analysis applications of lung analysis, coronary artery analysis, cardiac function analysis and calcification score is displayed. The user can select a desired menu item to cause the image interpretation workstation 2 to carry out the analysis application corresponding to the selected menu item.

Figure 6:
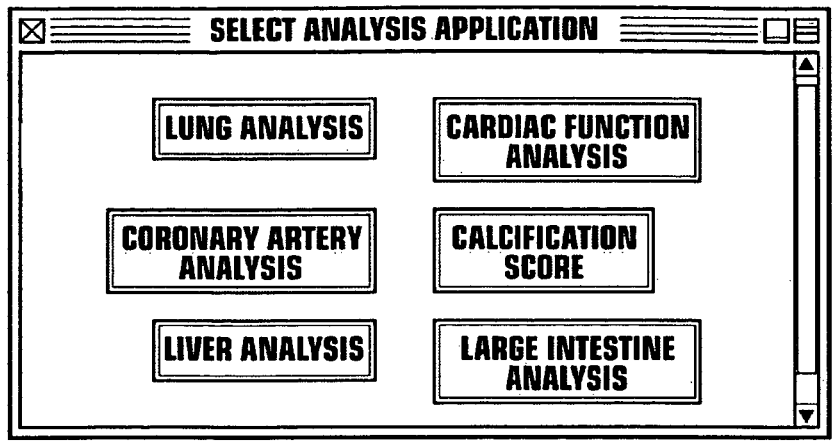
FIG. 6 is a diagram illustrating a state where a list of an analysis application menu is displayed in the first embodiment.

After the image has been selected on the examination list, a selection screen for selecting the specified analysis application maybe displayed, and a list of the menu of the analysis application(s) specified for the selected image may be displayed on the selection screen. FIG. 6 is a diagram illustrating a state where the list of the analysis application menu is displayed in the first embodiment. As shown in FIG. 6, in the case where the result of part recognition of the selected image is the chest and the abdomen, the analysis applications of lung analysis, coronary artery analysis, cardiac function analysis, calcification score, liver analysis and large intestine analysis are specified, and a list of an analysis application menu containing the analysis applications of lung analysis, coronary artery analysis, cardiac function analysis, calcification score, liver analysis and large intestine analysis is displayed on the selection screen. The user can select a desired menu item to cause the image interpretation workstation 2 to carry out the analysis application corresponding to the selected menu item.

Figure 7:
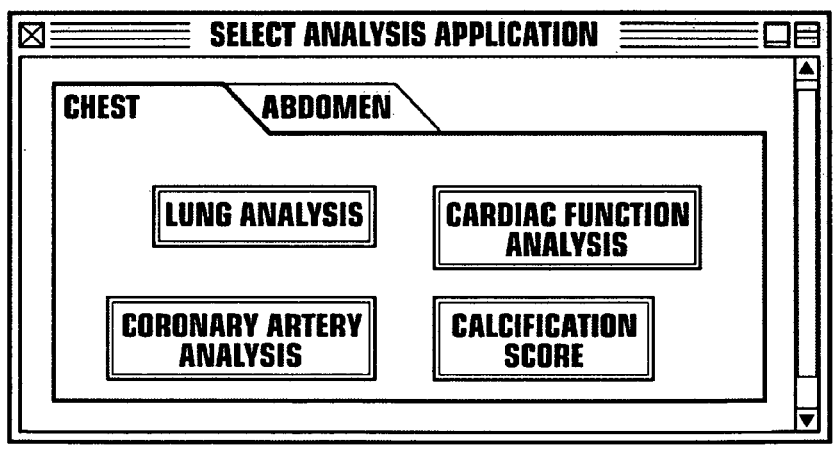
FIG. 7 is a diagram illustrating a state where a list of an analysis application menu for each part is displayed in the first embodiment.
Figure 8:
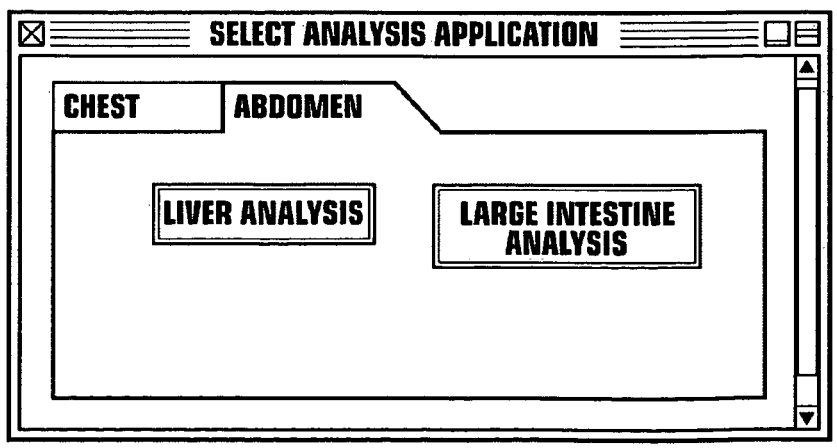
FIG. 8 is a diagram illustrating a state where another list of an analysis application menu for each part is displayed in the first embodiment.

Instead of displaying the list of the analysis applications, a list of analysis applications for each part may be displayed. For example, in the case where the result of part recognition of the selected image is the chest and the abdomen, tabs, as shown in FIG. 7, may be used to select the chest or the abdomen, and only a menu containing analysis applications corresponding to the selected part may be displayed. Namely, as shown in FIG. 7, when the tab for the chest is selected, a menu containing lung analysis, coronary artery analysis, cardiac function analysis and calcification score may be displayed, and when the tab for the abdomen is selected, as shown in FIG. 8, a menu containing liver analysis and large intestine analysis may be displayed. It is preferred to first display a part which spans across the largest distance along the body axis direction in the three-dimensional image.

As described above, in the first embodiment, an analysis application(s) depending on the part is specified from analysis applications used to display the three-dimensional image based on the result of part recognition of the three-dimensional image. Therefore, when an instruction to display the image is made, a menu containing only the specified analysis application(s) can be displayed, thereby allowing the user to select the analysis application from a menu containing only the analysis application(s) corresponding to the part contained in the three-dimensional image. Thus, it is not necessary for the user, such as a reading physician, to make selection from a menu that contains unnecessary menu items corresponding to parts that are not contained in the three-dimensional image, and thus a burden imposed on the user during menu selection can be reduced.

It should be noted that, although the part recognition terminal 5 carries out the part recognition process in the above-described embodiment, the image interpretation workstation 2 may carry out the part recognition process.

Next, a second embodiment of the invention is described. It should be noted that the medical information systems, to which the image processing devices according to the second and the following embodiments are applied, have the same configuration as that of the medical information system to which the image processing device according to the first embodiment is applied, and only the processes to be carried out are different. Therefore, detailed description of the configuration is omitted in the following description.

The user of the medical information system according to this embodiment is a reading physician, a technologist, or the like, and the analysis applications used at a clinical department, to which the user belongs, are almost fixed. For example, even for the same three-dimensional image of the chest, a reading physician at a cardiovascular department often uses analysis applications related to the heart, and a reading physician at a respiratory department often uses analysis applications related to the lung. Therefore, the difference between the first embodiment and the second embodiment lies in that, in the second embodiment, the analysis application(s) is specified based also on the user information. As the user information, not only information specifying a clinical department, such as cardiovascular department, respiratory department, department of digestive organs or brain surgery department, but also any information that is able to specify the user, such as a user ID to specify a reading physician or a technologist or an ID of the image interpretation workstation 2, may be used.

In the second embodiment, the image interpretation workstation 2 stores a table which associates, for each user information, each part contained in three-dimensional images with corresponding types of analysis application(s) used for analysis of the part. FIG. 9 is a diagram illustrating an example of a table used in the second embodiment. As shown in FIG. 9, a table T2 associates the chest with corresponding types of analysis applications for each clinical department. Specifically, the chest is associated with the cardiovascular department and the respiratory department. Further, the cardiovascular department is associated with the analysis applications of coronary artery analysis, cardiac function analysis and calcification score, and the respiratory department is associated with the analysis application of lung analysis. In the case where the table T2, as shown in FIG. 9, is used, the user inputs the name of the clinical department as the user information to the image interpretation workstation 2. Types of analysis applications to be used depending on the user information may be editable in the table T2 used in the second embodiment.

FIG. 10 is a diagram illustrating a state where a list of the analysis application menu is displayed in the second embodiment. In the case where the result of part recognition of the image selected by the user in the examination list shown in FIG. 4 represents the chest, the analysis applications of lung analysis, coronary artery analysis, cardiac function analysis and calcification score are specified. Then, if the user information represents the cardiovascular department, a list of an analysis application menu containing coronary artery analysis, cardiac function analysis and calcification score is displayed on a selection screen, as shown in a screen 20 in FIG. 10. On the other hand, if the user information represents the respiratory department, a list of an analysis application menu containing lung analysis is displayed on the selection screen, as shown in a screen 21 in FIG. 10. The user can select a desired menu item to cause the image interpretation workstation 2 to carry out the analysis application corresponding to the selected menu item.

As described above, in the second embodiment, the analysis application(s) is specified based also on the user information in addition to the result of part recognition. Therefore, when an instruction to display the image is made, a menu containing the analysis application(s) with a high frequency of use by the user is displayed, and thus a burden imposed on the user during menu selection can be reduced.

Next, a third embodiment of the invention is described. As described above, the modality 1 may include various systems, such as a CT system, an MRI system, a PET system, an SPET system and an ultrasonographic imaging system, and executable analysis applications differ depending on the type of the modality 1. The difference between the first embodiment and the third embodiment lies in that, in the third embodiment, in particular in the case where the medical information system includes two ore more modalities 1, the analysis application(s) is specified depending also on the type of the modality 1 contained in the associated information.

In the third embodiment, the image interpretation workstation 2 stores a table which associates, for each type of the modality 1 used to obtain the three-dimensional image, each part contained in the three-dimensional image with a corresponding type(s) of analysis application(s) used for analysis of the part. FIG. 11 is a diagram illustrating an example of a table used in the third embodiment. As shown in FIG. 11, a table T3 associates the chest with corresponding types of analysis applications for each type of the modality 1. Specifically, the chest is associated with a CT system and a MR system. Further, the CT system is associated with the analysis applications of coronary artery analysis, cardiac function analysis and calcification score, and the MR system is associated with the analysis applications of cardiac function analysis and delayed enhanced analysis.

FIG. 12 is a diagram illustrating a state where a list of the analysis application menu is displayed in the third embodiment. As shown in FIG. 12, in the case where the result of part recognition of the image selected by the user in the examination list shown in FIG. 4 represents the chest, if the modality 1 used to obtain the three-dimensional image is a CT system, the analysis applications of lung analysis, coronary artery analysis, cardiac function analysis and calcification score are specified. Then, as shown in a screen 22 in FIG. 12, a list of an analysis application menu containing coronary artery analysis, cardiac function analysis and calcification score is displayed on the selection screen. On the other hand, if the modality 1 used to obtain the three-dimensional image is a MR system, a list of an analysis application menu containing cardiac function analysis and delayed enhanced analysis is displayed on the selection screen, as shown in a screen 23 in FIG. 12. The user can select a desired menu item to cause the image interpretation workstation 2 to carry out the analysis application corresponding to the selected menu item.

As described above, in the third embodiment, the analysis application(s) is specified based also on the type of the modality 1 used to obtain the three-dimensional image, in addition to the result of part recognition. Therefore, when an instruction to display the image is made, the analysis application(s) which is highly likely to be applied to the displayed three-dimensional image is displayed, and thus a burden imposed on the user during menu selection can be reduced.

Next, a fourth embodiment of the invention is described. The difference between the first embodiment and the fourth embodiment lies in that, in the fourth embodiment, the image interpretation workstation 2 records a log of the number of use of each analysis application, and when the image interpretation is instructed by the user at the image interpretation workstation 2, the image interpretation workstation 2 specifies the analysis application(s) depending on the part contained in the three-dimensional image, and change the manner of display of the analysis application menu so that the analysis application(s) with a higher frequency of use can more easily be selected.

Figure 13:
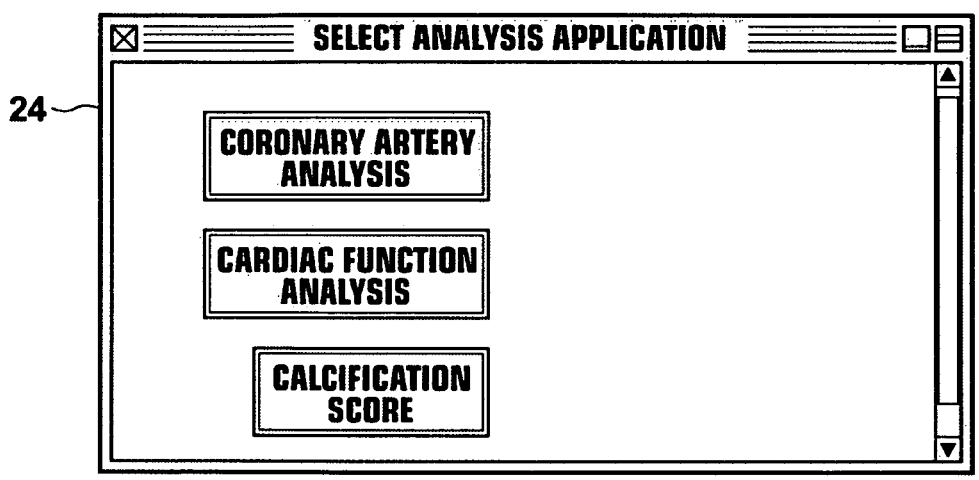
FIG. 13 is a diagram illustrating a state where a list of an analysis application menu is displayed in the second embodiment.
Figure 14:
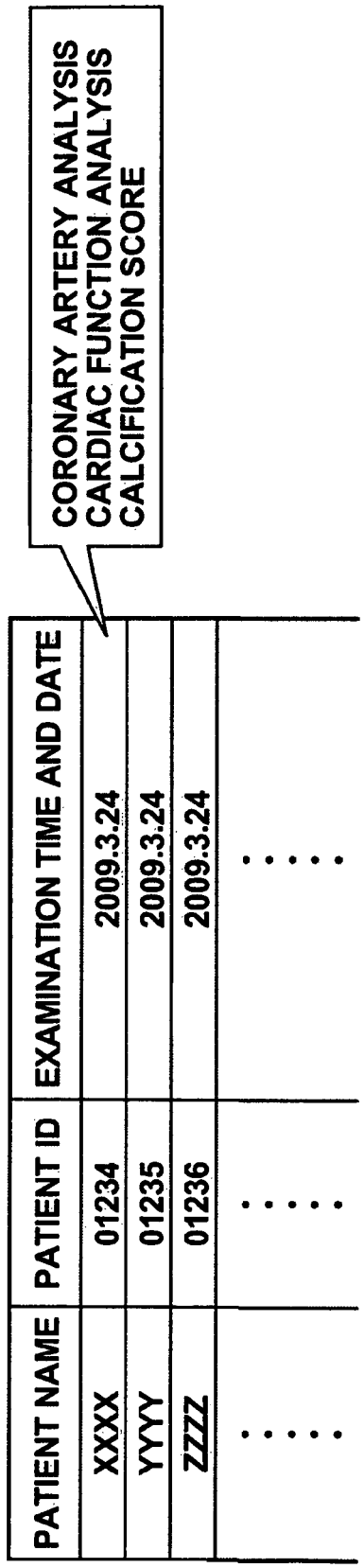
FIG. 14 is a diagram illustrating a state where a pop-up of an analysis application menu is displayed in a fourth embodiment.

FIG. 13 is a diagram illustrating a state where a list of the analysis application menu is displayed in the fourth embodiment. In the following description, it is assumed that analysis applications of coronary artery analysis, cardiac function analysis and calcification score are specified based on the information of the result of part recognition, and the frequencies of use of the analysis applications are in the order of coronary artery analysis, cardiac function analysis and calcification score. In this case, as shown in a screen 24 in FIG. 13, a list of an analysis application menu containing coronary artery analysis, cardiac function analysis and calcification score is displayed with these menu items arranged in this order from the top. In the case where a pop-up of the analysis application menu is displayed, a pop-up of the analysis application menu containing coronary artery analysis, cardiac function analysis and calcification score is displayed with these menu items arranged in this order from the top, as shown in FIG. 14.

Figure 15:
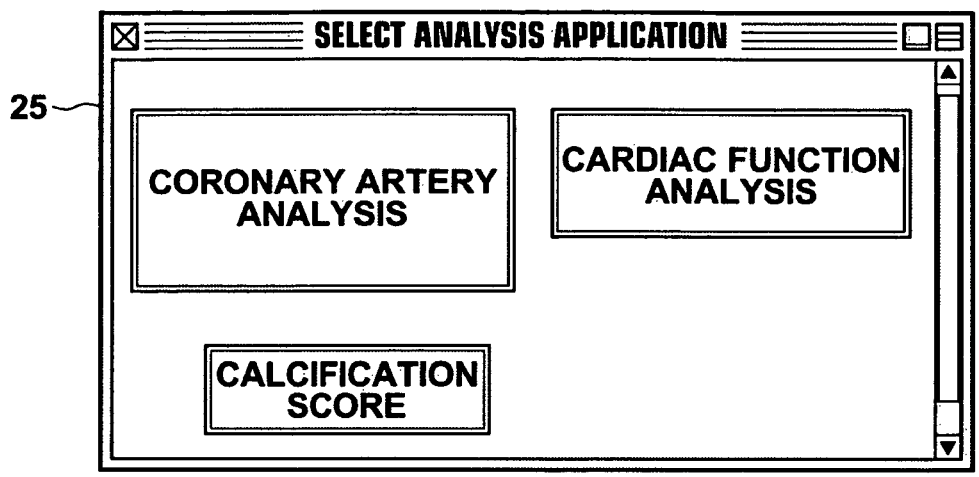
FIG. 15 is a diagram illustrating a state where another list of the analysis application menu is displayed in the fourth embodiment.
Figure 16:
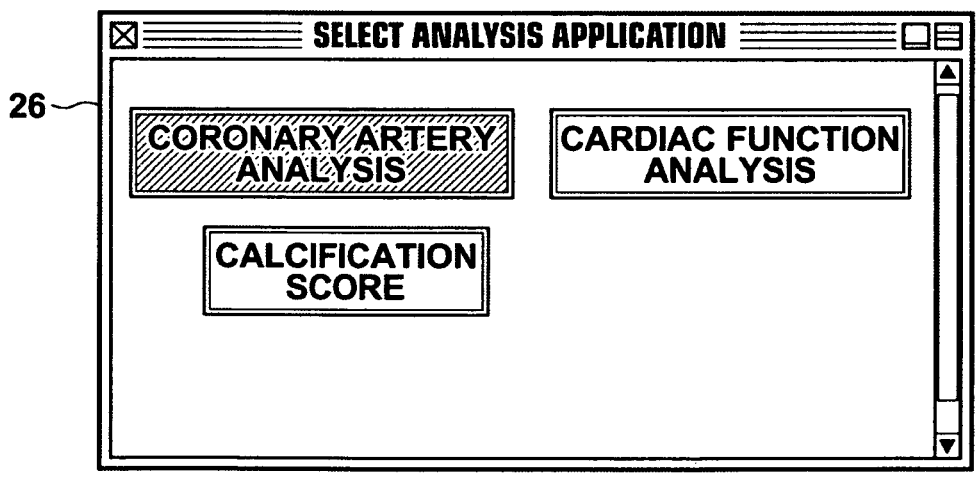
FIG. 16 is a diagram illustrating a state where still another list of the analysis application menu is displayed in the fourth embodiment.

Further, as shown in a screen 25 in FIG. 15, menu items of the analysis applications may be displayed such that the menu item of the analysis application with a higher frequency of use is provide with a larger size. Furthermore, as shown in a screen 26 in FIG. 16, when the list of the analysis application menu is displayed, an icon of the coronary artery analysis with the highest frequency of use may be displayed in a selected state. In FIG. 16, the hatched menu item represents the selected state. This allows the user to execute the analysis application with the highest frequency of use only by pressing the execution key of the input device, such as a keyboard, of the image interpretation workstation 2.

As described above, in the fourth embodiment, the manner of display of the analysis application menu is changed so that the analysis application with a higher frequency of use of the specified analysis applications can more easily be selected, and thus a burden imposed on the user during menu selection can be reduced.

It should be noted that, in the third embodiment, in particular in the case where a three-dimensional image obtained with a CT system and a three-dimensional image obtained with an SPET system are send to the image interpretation workstation 2 as three-dimensional images of the same patient, and if the result of part recognition is the chest and the three-dimensional image obtained with the CT system is selected as the image to be displayed, the purpose of the three-dimensional image is not diagnosis of the lung, but diagnosis of the cardiac function. Therefore, in this case, the manner of display of the analysis application menu may be changed so that the analysis application of cardiac function analysis, which is highly likely to be used, can more easily be selected.

Next, a fifth embodiment of the invention is described. In the case where the three-dimensional image is displayed in a manner of the above-described MIP display or VR display, diagnosis can be facilitated by changing a shading pattern of bone, flesh, organ, etc., depending on the part. The difference between the first embodiment and the fifth embodiment lies in that, in the fifth embodiment, color templates corresponding to the result of part recognition is specified from a plurality of color templates for changing the shading pattern of the three-dimensional image depending on the result of part recognition, and a list of a menu for selecting a color template from the specified color templates is displayed so that selection is carried out only from the specified color templates.

Figures 17, 18:
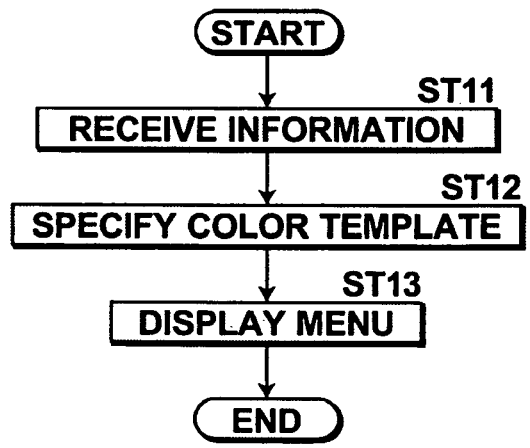
FIG. 17 is a diagram illustrating an example of a table used in a fifth embodiment.
FIG. 18 is a flow chart illustrating a process carried out in the fifth embodiment.

It should be noted that the image interpretation workstation 2 stores a table which associates each part contained in the three-dimensional image with types of color templates to be used to three-dimensionally display the part. FIG. 17 is a diagram illustrating an example of a table used in the fifth embodiment. As shown in FIG. 17, a table T4 associates each part with the types of color templates. Specifically, the head is associated with color templates P1-P5, the neck is associated with color templates P6-P10, the chest is associated with color templates P11-P20, the chest-abdomen is associated with color templates P21-P25, the abdomen is associated with color templates P26-P30, and the pelvis is associated with color template P31-P35.

In the fifth embodiment, when the user performs image interpretation, the image interpretation workstation 2 first obtains the associated information and the information of the result of part recognition for each examination, in response to an instruction from the user. Then, the color templates are specified depending on the part contained in the three-dimensional image with referencing the table T4 based on the information of the result of part recognition, and the specified color templates are displayed on the display.

Next, a process carried out in the fifth embodiment is described. FIG. 18 is a flow chart illustrating the process carried out in the fifth embodiment. The process described here includes operations that are carried out after the information of the result of part recognition has been registered in the image database 4, and the user, such as a reading physician, has fed an instruction of image interpretation to the image interpretation workstation 2, and until the specified color templates are displayed. When the user has fed the instruction of image interpretation to the image interpretation workstation 2, the image server 3 reads out a registered three-dimensional image together with the associated information and the information of the result of part recognition thereof from the image database 4, and sends the three-dimensional image, the associated information and the information of the result of part recognition to the image interpretation workstation 2.

The image interpretation workstation 2 receives the three-dimensional image, the associated information and the information of the result of part recognition ("receive information" in step ST11). Then, based on the received information of the result of part recognition, the color templates are specified depending on the part contained in the three-dimensional image with referencing the above-described table T4 (step ST12). Then, a menu containing the specified color templates is displayed together with the three-dimensional image (step ST13), and the process ends.

Figure 19:
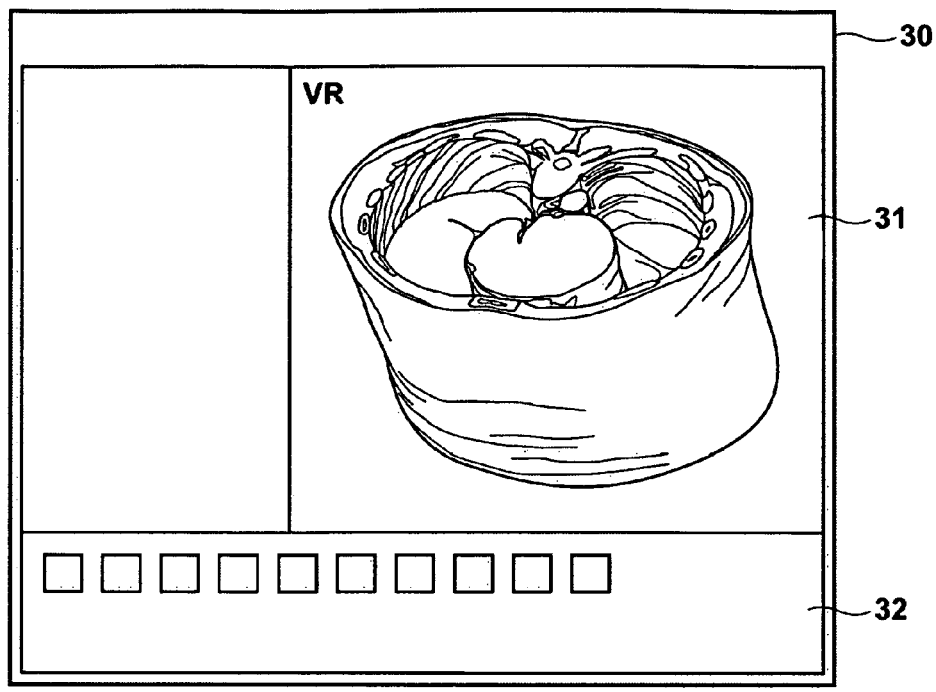
FIG. 19 is a diagram illustrating a screen displayed in the fifth embodiment.

FIG. 19 is a diagram illustrating a displayed screen in the fifth embodiment. As shown in FIG. 19, the screen 30 includes a VR image 31 and a color template display area 32 displayed thereon. In the color template display area 32, a menu containing the specified color templates is displayed. For example, if the VR image 31 is an image of the chest, the specified part is the chest, and therefore the color templates P11-P20 are displayed in the color template display area 32 with referencing the table T4. In FIG. 19, menu items of the color templates are displayed in the form of rectangular icons. Each menu item is displayed such that a part to be specified, a state of the shading of the part, etc., are recognizable by the user. The user can select a desired color template on the screen 30 to impart a desired shading pattern to the VR image 31.

As described above, in the fifth embodiment, the color templates used to display the three-dimensional image are specified depending on the result of part recognition. Therefore, when an instruction to display the image is made, the color templates to be used only with the displayed three-dimensional image are displayed, and thus a burden imposed on the user during selection of the color template can be reduced.

It should be noted that, in the above-described fifth embodiment, all the available color templates may be displayed, and only the specified color templates may be displayed to be more easily selected, such as by reducing the density of the color templates other than the specified color templates.

Further, in the fifth embodiment, the image interpretation workstation 2 may record a log of the number of use of each color template, and may change the manner of display of the color template menu when the three-dimensional image is displayed so that the color template with a higher frequency of use can more easily be selected. For example, a menu containing only the color templates having a frequency of use not less than a predetermined threshold may be displayed, a menu may be displayed with rearranging the color templates contained therein in the order of the frequency of use, or a menu item of the color template with a higher frequency of use may be provided with a larger size.

Figure 20:
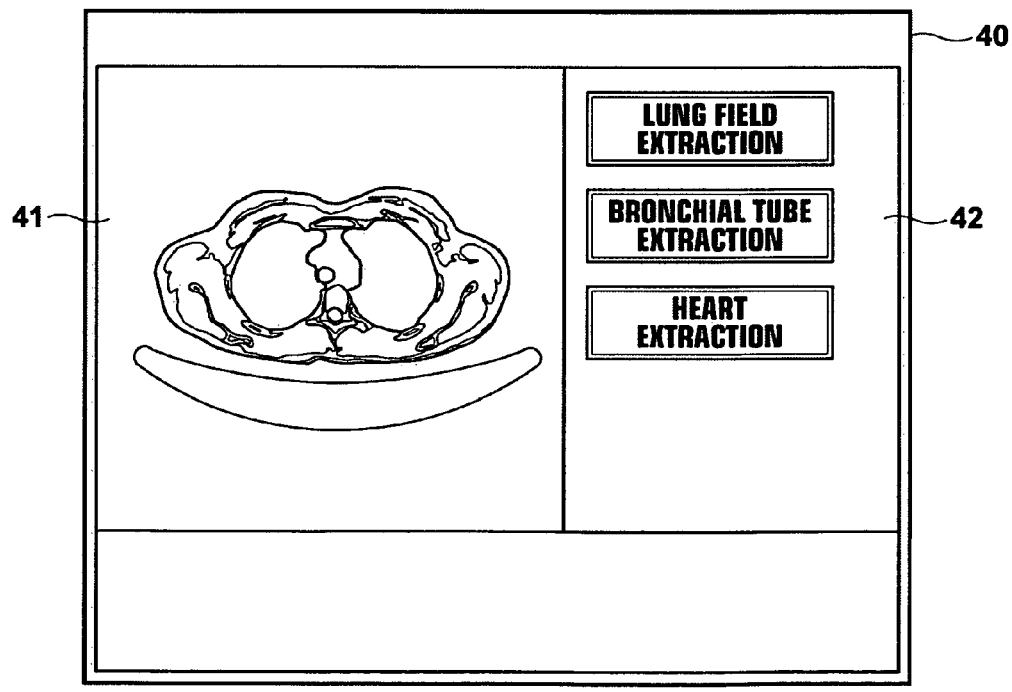
FIG. 20 is a diagram illustrating another screen displayed in the fifth embodiment.

It should be noted that, besides the analysis applications, applications necessary for image interpretation, such as image processing applications and display applications, are installed on the image interpretation workstation 2. Therefore, menus displayed depending on the part at the image interpretation workstation 2 are not limited to those containing the analysis applications and the types of color templates, but may also include other menus for executing image processing applications and display applications installed on the image interpretation workstation 2. For example, if the part of the three-dimensional image to be displayed is the chest, image processing applications for lung field extraction, bronchial tube extraction, heart extraction, etc., may often be executed. Therefore, when an axial image 41 of the chest, for example, is displayed, as shown in a screen 40 in FIG. 20, only a menu containing image processing applications for lung field extraction, bronchial tube extraction and heart extraction may be displayed in a menu display area 42.

Further, although the menu is specified depending on the result of part recognition in the above-described embodiments, a part of interest in the displayed image may be recognized and the menu may be specified depending on the result of the part recognition of the part of interest. For example, with respect to an image of the chest, a cut in the chest may be opened through operation of the input device of the image interpretation workstation 2, and the manner of display of the three-dimensional image may be changed so that the lung fields and the heart present at deeper positions from the skin surface can more easily be seen. Specifically, in the case where the input device is a touch panel, the image may be displayed as if the cut is opened when the user touches the touch panel and makes a gesture of opening fingers, and the manner of display may be changed so that the lung fields and the heart present at deeper positions from the skin can be seen. In this case, the image interpretation workstation 2 may recognize the part of interest, and the menu may be specified depending on the result of part recognition of the part of interest to display the specified menu.

Furthermore, the three-dimensional image may be displayed in a manner of VR display, MIP display, MinIP display, or the like, and the manner of display of a menu of these display applications may be changed depending on the result of part recognition. That is, since a display application to be used differs depending on the part, the manner of display of the menu may be changed so that a menu item of the display application highly likely to be used with the displayed part can more easily be selected. For example, the MinIP display is often used to observe the lung fields. Therefore, if an image of the chest or an image of the chest-abdomen is displayed, the menu may be displayed depending on the result of part recognition so that a menu item for carrying out the MinIP display can more easily be selected. In the case where bone reduction processing is applied to an image of the chest, it is highly likely that the MIP display is carried out. Therefore, the manner of display of the display menu may be changed so that a menu item of the display application can more easily be selected with taking a result of image processing applied to the image into account.

It should be noted that a multi-touch panel, which can accept input touches made at two or more positions on the screen, may be used as the input device of the image interpretation workstation 2. Even in this case, the menu can be specified depending on the result of part recognition.

What is claimed is:

1. An image processing device comprising:
    a display unit for displaying an image;
    an image obtaining unit for obtaining a three-dimensional image, the three-dimensional image comprising a plurality of tomographic images obtained by carrying out tomographic imaging of a subject;
    a body part information obtaining unit for obtaining information of a result of body part recognition of a particular body part included in the image displayed on the display unit from among a plurality of body parts of the subject contained in the three-dimensional image;
    a menu specifying unit for specifying, from a plurality of menus used to display the three-dimensional image and for selecting an image processing application for extracting an organ, a menu depending on the particular body part based on the information of the result of body part recognition; and
    a display control unit for displaying the specified menu on a menu display means,
    wherein the specified menu displayed on the menu display means includes determined image processing applications based on the particular body part included in the image displayed on the display unit from among the plurality of body parts of the subject contained in the three-dimensional image.

2. The image processing device as claimed in claim 1, wherein the menu specifying unit specifies the menu depending also on user information of a user who uses the three-dimensional image.

3. The image processing device as claimed in claim 1, wherein the menu specifying unit specifies the menu depending also on a type of a modality used to obtain the three-dimensional image.

4. The image processing device as claimed in claim 1, wherein the display unit is combined with a touch panel input device; and
   wherein the display control unit changes a manner of display of the image displayed on the display unit based on the input of the touch panel input device.

5. The image processing device as claimed in claim 1, wherein the body part information obtaining unit obtains information of a result of body part recognition of an axial image displayed on the display unit.

6. An image processing method to be implemented on a computer, comprising the steps, which are carried out by the computer, of:
   obtaining a three-dimensional image, the three-dimensional image comprising a plurality of tomographic images obtained by carrying out tomographic imaging of a subject;
   obtaining information of a result of body part recognition of a particular body part included in the image displayed on a display unit from among a plurality of body parts of the subject contained in the three-dimensional image;
   specifying, from a plurality of menus used to display the three-dimensional image and for selecting an image processing application for extracting an organ, a menu depending on the particular body part based on the information of the result of body part recognition; and
   displaying the specified menu on a menu display means,
   wherein the specified menu displayed on the menu display means includes determined image processing applications based on the particular body part included in the image displayed on the display unit from among the plurality of body parts of the subject contained in the three-dimensional image.

7. An image processing apparatus comprising at least one processor for running a program for causing a computer to carry out the procedures of:
   obtaining a three-dimensional image, the three-dimensional image comprising a plurality of tomographic images obtained by carrying out tomographic imaging of a subject;
   obtaining information of a result of body part recognition of a particular body part included in the image displayed on a display unit from among a plurality of body parts of the subject contained in the three-dimensional image;
   specifying, from a plurality of menus used to display the three-dimensional image and for selecting an image processing application for extracting an organ, a menu depending on the particular body part based on the information of the result of body part recognition; and
   displaying the specified menu on a menu display means;
   wherein the specified menu displayed on the menu display means includes determined image processing applications based on the particular body part included in the image displayed on the display unit from among the plurality of body parts of the subject contained in the three-dimensional image.

* * * * *